US008993984B2

(12) United States Patent
Gord et al.

(10) Patent No.: US 8,993,984 B2
(45) Date of Patent: Mar. 31, 2015

(54) ALL FIBER COUPLED ULTRAVIOLET PLANAR LASER INDUCED FLUORESCENCE DETECTION SYSTEM

(71) Applicant: Government of the United States, as represented by the Secretary of the Air Force, Wright-Patterson AFB, OH (US)

(72) Inventors: James R Gord, Beavercreek, OH (US); Sukesh Roy, Beavercreek, OH (US); Paul Hsu, Beavercreek, OH (US); Waruna Kulatilaka, Beavercreek, OH (US)

(73) Assignee: The United States of America as represented by the Secretary of the Air Force, Washington, DC (US)

( * ) Notice: Subject to any disclaimer, the term of this patent is extended or adjusted under 35 U.S.C. 154(b) by 133 days.

(21) Appl. No.: 13/858,995

(22) Filed: Apr. 9, 2013

(65) Prior Publication Data
US 2013/0270458 A1     Oct. 17, 2013

Related U.S. Application Data

(60) Provisional application No. 61/623,228, filed on Apr. 12, 2012.

(51) Int. Cl.
*G01N 21/64* (2006.01)
(52) U.S. Cl.
CPC .......... *G01N 21/645* (2013.01); *G01N 21/6402* (2013.01); *G01N 2201/08* (2013.01)
USPC ....................... 250/461.1; 436/140
(58) Field of Classification Search
CPC ....................................... G01N 21/64
USPC ....................... 250/461.1; 436/140
See application file for complete search history.

(56) References Cited

U.S. PATENT DOCUMENTS

| 4,799,754 | A | * | 1/1989 | Goldenberg | 385/33 |
| 5,579,166 | A | | 11/1996 | Beiting | |
| 5,751,871 | A | * | 5/1998 | Krivoshlykov et al. | 385/33 |
| 6,385,380 | B1 | * | 5/2002 | Friedrich et al. | 385/125 |
| 6,856,713 | B2 | | 2/2005 | Nelson et al. | |
| 7,064,329 | B2 | | 6/2006 | Webber | |
| 2003/0038237 | A1 | | 2/2003 | Webber | |
| 2003/0059950 | A1 | * | 3/2003 | Simeonsson | 436/182 |
| 2006/0194334 | A1 | * | 8/2006 | Zhang | 436/172 |
| 2010/0068821 | A1 | * | 3/2010 | St. Germain | 436/140 |

OTHER PUBLICATIONS

Stanjan Chemical Equilibrium Calculator, http://navier.engr.colostate.edu/~dandy/code/code-4/index.html.
Meyer et al., "Measurements of OH mole fraction and temperature up to 20 kHz by using a diode-laser-based UV absorption sensor," Appl. Opt., vol. 44, pp. 6729-6740, 2005.
Klein et al., "Fiber-guided tunable UV-laserlight system around 215 nm," Proc. SPIE 2977, 94,1997.

* cited by examiner

*Primary Examiner* — David Porta
*Assistant Examiner* — Meenakshi Sahu
(74) *Attorney, Agent, or Firm* — AFMCLO/JAZ; Charles Figer, Jr.

(57) ABSTRACT

A high energy UV fiber-coupled laser-induced fluorescence system is provided having a transmission component and a receiving component. The transmission component includes a laser source configured to produce high-energy UV pulses, a UV-enhanced fused-silica fiber coupled to the laser source, and optics coupled to the UV-enhanced fused-silica fiber for transmitting the high-energy UV pulses to a target area. The receiving component receives laser-induced florescence events from the target area and includes additional UV-enhanced fused-silica fiber coupled to optics and a receiving means.

14 Claims, 5 Drawing Sheets

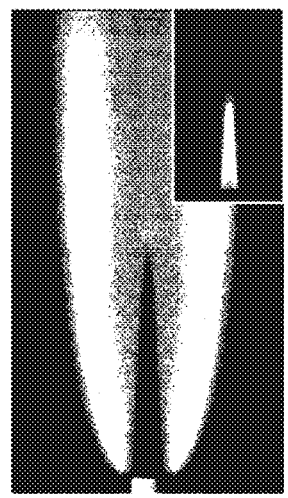 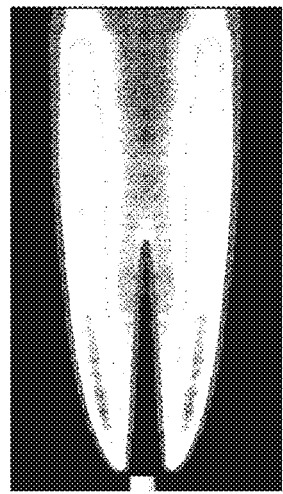
FIG. 8A    FIG. 8B
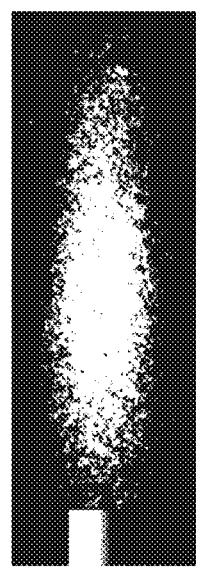 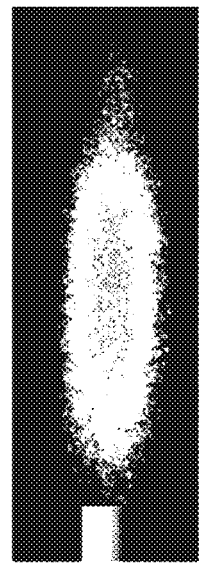
FIG. 9A    FIG. 9B

ALL FIBER COUPLED ULTRAVIOLET PLANAR LASER INDUCED FLUORESCENCE DETECTION SYSTEM

CROSS-REFERENCE TO RELATED APPLICATIONS

This application claims the benefit of and priority to U.S. Provisional Application Ser. No. 61/623,228, entitled "Development of an all-fiber coupled, ultraviolet, planar-laser-induced-fluorescence (UV-PLIF) detection system," filed on Apr. 12, 2012, the entirety of which is incorporated by reference herein.

RIGHTS OF THE GOVERNMENT

The invention described herein may be manufactured and used by or for the Government of the United States for all governmental purposes without the payment of any royalty.

BACKGROUND OF THE INVENTION

1. Field of the Invention

The present invention generally relates to laser-induced fluorescence and, more particularly, to fiber-coupled laser-induced fluorescence systems.

2. Description of the Related Art

The development of laser-induced fluorescence (LIF) as a combustion-diagnostic technique has permitted spatially resolved species-concentration and temperature measurements in reacting flows. LIF has particular advantages over other laser-diagnostic techniques because of its high detection sensitivity and excellent spatial resolution, which permit accurate measurements of minor species that play a critical role in chemical-kinetics mechanisms in reacting flows. Typical examples of such minor species are OH, CH, NH, and CN radicals as well as atomic species such as H and O. LIF also provides a straightforward, single-beam diagnostic approach that is experimentally less complicated than other Raman-based and wave-mixing techniques that require multiple laser beams for excitation. Furthermore, LIF can easily be extended to two-dimensional measurements using planar LIF (PLIF). Two-line OH-LIF has been demonstrated for thermometry in reacting flows. PLIF of tracer molecules has been used for mixture-fraction imaging and mixing studies in nitrogen-helium flows, where a non-fluorescing fuel is doped with a fluorescing tracer having ultraviolet (UV) excitation bands. Also, PLIF of seeded NO has been employed for pressure, temperature, and velocity measurements in supersonic and hypersonic flows. LIF has also been used to detect hydrocarbon species such as benzene, toluene, xylene, and ethylbenzene as well as polycyclic aromatic hydrocarbons (PAHs). A common spectroscopic feature of all of the aforementioned species is that their molecular transitions from the ground electronic state to the first excited state lie in the UV wavelength regime (200-450 nm), which requires that any laser-based spectroscopic technique must utilize UV lasers for excitation.

Traditional LIF techniques, which were developed to aid the understanding of fundamental combustion chemistry and dynamics in well-controlled laboratory flames, face a stiff challenge when implemented in practical combustion devices such as combustors and afterburners in practical gas-turbine engines. These harsh combustion environments are often associated with 1) extreme heat and vibrations, 2) unconditioned humidity and large thermal gradients, and 3) little or no optical access, which severely affects the free-standing optics used in traditional LIF measurements. These difficulties may be resolved by transmitting the required laser energy through optical fibers to a test section, with the laser system and detection hardware being located in an adjacent climate-controlled room. In particular, a fiber-coupled UV-LIF system would 1) reduce the need for standing optics in the test-cell environment, 2) ease the alignment of multiple laser beams, providing flexibility when needed and the ability to access non-windowed test sections, 3) isolate the high-power laser system from harsh environments, and 4) provide safe, guided, and confined laser delivery.

For long distance delivery of high-power laser pulses, the optimum fiber is fused-silica, solid-core fiber because absorption and bending loss are minimal. Some fiber-coupled UV-LIF systems have been developed using such a fiber for detection of petroleum products and biological samples in condensed phases. These systems have shown that the required pulse energy for LIF in condensed phases is considerably below the damage threshold of the fiber. However, in gas-phase media, because of the lower molecular densities, the effective optical depth is reduced by several orders of magnitude and, hence, the laser pulse energy required for LIF signal generation is at least one order of magnitude higher than that required for the condensed phase. Recently, UV-LIF of atmospheric OH and $HO_2$ has been achieved through the use of multi-pass white cells for weak LIF signal enhancement. But, such a system has limited application in combustion and non-reacting flow diagnostics where measurements need to be performed without perturbing the system under study. A primary challenge in the development of a high-temperature, gas-phase, fiber-coupled UV-LIF system involves the delivery of sufficient laser energy through the fibers. Additional difficulties arise when the excitation laser beam is in the UV regime, where the transmission characteristics of UV laser pulses in silica fibers (e.g., transmission efficiency) degrade because of a solarization effect. Solarization is caused by the absorption of UV energy by silica material and results in a change in the transmission properties caused by the formation of defect centers that further reduce transmission and generate new wavelengths.

Accordingly, as a result of the technical barriers described above, there is a need in the art for a fiber-coupled UV-LIF system for gas-phase reacting-flow applications.

SUMMARY OF THE INVENTION

Embodiments of the invention provide a high energy UV fiber-coupled laser-induced fluorescence system. These embodiments include a transmission component and a receiving component. The transmission component includes a laser source configured to produce high-energy UV pulses, UV-enhanced fused-silica fiber coupled to the laser source, and optics coupled to the first UV-enhanced fused-silica fiber for transmitting the high-energy UV pulses to a target area. The receiving component receives laser-induced florescence events from the target area and includes optics, UV-enhanced fused-silica fiber coupled to the optics, and a receiving means coupled to the second UV-enhanced fused-silica fiber. In some embodiments, the UV-enhanced fused-silica fibers have a length on the order of meters. In these embodiments, the UV-enhanced fused-silica fibers are able to maintain a transmission of high-power, 10-Hz, deep UV (283 nm) laser pulses at an intensity of approximately $10 \times 10^6$ W/cm$^2$ through a 10-m-long FDP fiber over 10,000 pulses (or 15 minutes continuous irradiation.

In some embodiments, the receiving means may include a bandpass filter and photomultiplier tube, an ICCD camera, and combinations thereof. In these embodiments, the laser source may include a dye laser. In some embodiments, the laser source may also include a Nd:YAG laser coupled to the dye laser and configured to pump the dye laser. In a particular embodiment, the laser source may also include a frequency doubler configured to double an output of the dye laser.

In some embodiments, the UV-enhanced fused-silica fiber is coupled to the laser source by a coupling including a diffractive optical element diffuser and a fiber end-cap coupled with the diffractive optical element diffuser. In some of these embodiments, the coupling further includes a lens positioned between the diffractive optical element diffuser and the fiber end cap. Some embodiments utilize fiber in the form of a plurality of UV-enhanced fused-silica fibers configured as a bundle. In some of these embodiments, the plurality of UV-enhanced fused-silica fibers at an end of the bundle are formed into a linear array.

The receiving component for some embodiments includes a probe coupled to an end of the bundle of the plurality of UV-enhanced fused-silica fibers receiving the laser-induced florescence events from the target area. The probe has coupling optics directing the laser-induced florescence events at the plurality of UV-enhanced fused-silica fibers, and, in some embodiments, active cooling integrated in the probe. In some of these embodiments, the probe further includes thermal blanketing to protect against the harsh environments.

Additional objects, advantages, and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

BRIEF DESCRIPTION OF THE DRAWINGS

The accompanying drawings, which are incorporated in and constitute a part of this specification, illustrate embodiments of the invention and, together with a general description of the invention given above, and the detailed description given below, serve to explain the invention.

FIGS. 8A and 8B are exemplary OH-PLIF images acquired by fiber coupled PLIF;

FIGS. 9A and 9B are exemplary NO-PLIF images acquired by fiber coupled PLIF.

Figure 1:
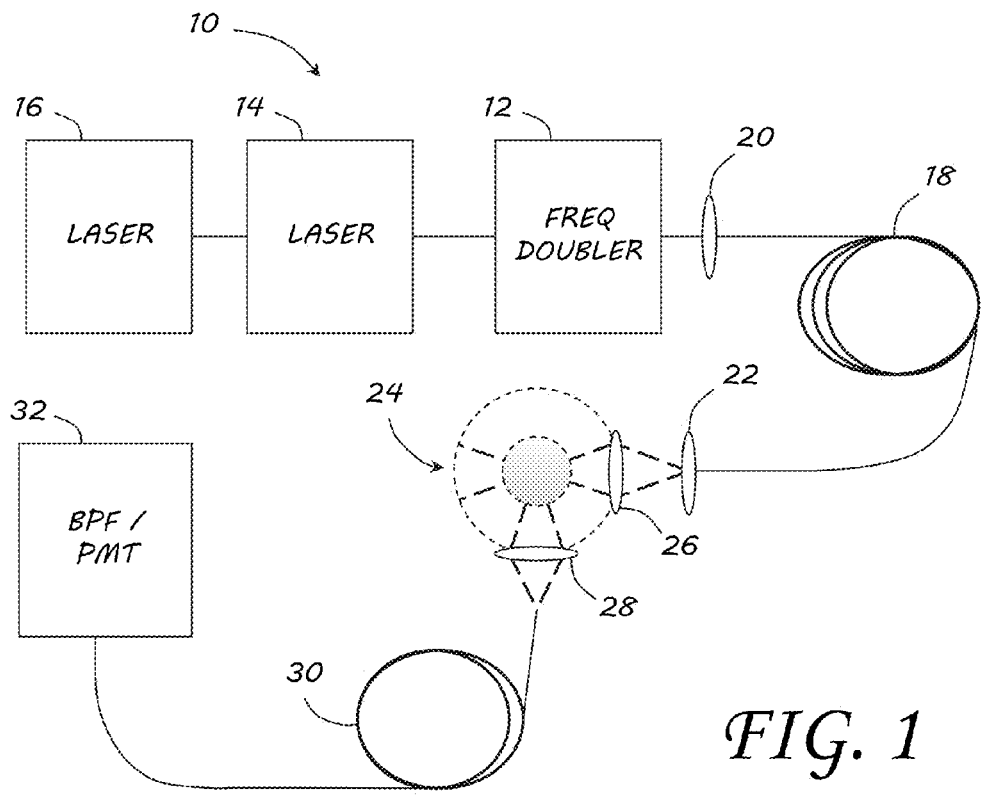
FIG. 1 is a schematic drawing of an exemplary apparatus for an all-fiber-coupled LIF detection system consistent with embodiments of the invention.

It should be understood that the appended drawings are not necessarily to scale, presenting a somewhat simplified representation of various features illustrative of the basic principles of the invention. The specific design features of the sequence of operations as disclosed herein, including, for example, specific dimensions, orientations, locations, and shapes of various illustrated components, will be determined in part by the particular intended application and use environment. Certain features of the illustrated embodiments have been enlarged or distorted relative to others to facilitate visualization and clear understanding. In particular, thin features may be thickened, for example, for clarity or illustration.

DETAILED DESCRIPTION OF THE INVENTION

Laser-induced fluorescence (LIF) is the optical fluorescence from molecules that have been excited from a ground state to an upper excited state via absorption of laser photons. Thus, in a linear LIF regime, the LIF signal strength is linearly proportional to the number of laser photons delivered during the duration of the pulse. Therefore, higher pulse energy is favorable for increasing the detection signal-to-noise ratio (SNR). Additionally, the narrow input-pulse bandwidth is desired for accurate and sensitive LIF measurements. Thus, retention of the input-pulse bandwidth during beam propagation through the fiber is essential for a fiber-coupled UV-LIF detection system. Furthermore, a reasonable spatial resolution for a fiber-coupled UV-LIF system is required for achieving accurate species-concentration and temperature measurements at a "point." The spatial resolution of a fiber-coupled UV-LIF system depends on the focal spot size in the probe volume, which is dependent on the quality of the beam. Thus, a high-quality beam is critical to the accuracy of point measurements. Hence, the design and performance of a fiber-coupled UV-LIF system for temperature and species-concentration measurements are determined by three vital parameters:

(1) delivery of high-energy/irradiance UV pulses for LIF measurements in reacting flows,
(2) delivery of high beam quality at the probe volume, and
(3) retention of the bandwidth of the input pulse during propagation through the fiber.

An all-fiber-coupled UV-PLIF detection system embodiment of the invention was tested for probing hydroxyl radical (OH) and nitric oxide (NO) in premixed flames and in a room-temperature NO-seeded N2 jet. From these tests, four merits of the developed all-fiber-coupled UV-PLIF system embodiments as a diagnostics tool for LIF-based measurements in harsh combustion environments were identified:

First, a fiber-coupled beam delivery system is capable of transmitting sufficient UV laser pulse energy for performing high temperature gas-phase PLIF measurements at a rate if either 10 Hz or 10 kHz. This may be accomplished in some embodiments with long length fibers (up to 10 m) that facilitate sufficient flexibility for application in practical diagnostic environments. Second, a similar order of LIF measurement accuracy was obtained using the all-fiber-coupled PLIF system as compared to the conventional free-standing optics (no fiber) LIF. Third, a nearly uniform output-beam profile from the fiber-optics beam delivery system may be very useful for PLIF measurements. And, fourth, efficient signal collection is achieved through fiber-optic fluorescence collection system with a long-length fiber.

A schematic 10 of an all-fiber-coupled PLIF detection system embodiment of OH is shown in FIG. 1. A 10-Hz, 8-ns-duration, 283 nm laser beam for OH excitation was generated by frequency doubling 12 an output of a narrowband dye laser 14, such as a ND6000 Dye Laser from Continuum, Inc. of Santa Clara, Calif., that was pumped by a second harmonic (532 nm) of a a-switched Nd:YAG laser 16, such as a Spectra Physics PR0350 Nd:YAG laser from Newport Corporation of Irvine, Calif. The output of the frequency-doubled dye laser produces narrowband pulses, with beam quality of $M^2$ at approximately 10. $M^2$ is determined by the ratio of the beam-parameter product (BPP) of a real beam to that of a diffraction-limited beam at the same laser wavelength ($\lambda$) using the formula:

$$M^2 = \frac{d_0 \alpha_0}{\left(\frac{4\lambda}{\pi}\right)} \quad (1)$$

where $d_0$ is the beam diameter at focus, and $\alpha_0$ is the full divergence angle. If $\alpha_0$ of the fiber-delivered beam is close to that of the diffraction-limited beam, then $M^2$ can be estimated to be the ratio of the focal-spot diameter of the fiber-delivered beam to that of the diffraction-limited beam (i.e., $M^2 \sim d_0/d_{diff}$). This beam is then coupled to a 400-μm-core deep-UV-enhanced fused-silica fiber 18, such as FDP400440480 from Polymicro Technologies of Phoenix, Ariz., a subsidiary of Molex, Inc., using an f=+150-mm spherical lens 20. This fiber 18 was experimentally identified as being a suitable commercial fiber for a fiber-coupled UV-LIF system because of its ability to resist solarization effects, though other fibers with similar properties may also be used in other embodiments. In a particular embodiment, the fused-silica fiber 18 may include a core having high-purity silica glass containing OH-groups in the amount of approximately 0.1 to approximately 10.0 ppm and chlorine in the amount of less than approximately 1000 ppm. The fused-silica fiber 18 may also include a cladding surrounding the core having high-purity silica glass containing fluorine and having a refractive index less than a refractive index of the core. The fused-silica fiber 18 may additionally be treated in hydrogen gas to remove intrinsic and impurity defects. The end faces of the fiber 18 are finely polished and equipped with special designed high-power connector available from Polymicro Technologies, for example, thereby reducing heat load from the laser injection in fiber tip and hence, increasing the fiber damage threshold. The fiber 18 was placed in a six-axis kinematic mount, which was attached to a one dimensional translational stage that moved along a direction of laser beam propagation. An input end of the fiber 18 was positioned behind a focal point of the lens 20 such that the beam expanded to fill approximately 65 percent of the core area. This placement assisted in reducing laser intensity at the input surface of the fiber 18, thereby avoiding damage to the fiber surface, and also provided for a margin of error in a transverse alignment of the fiber 18. The fiber input facet was observed using a camera microscope to optimize the transverse alignment of the laser beam relative to the center of the fiber core.

The output of the fiber 18 is collimated by employing another f=+150 mm spherical lens 22 and focused onto the probe volume 24 using an f=+100 mm spherical lens 26. A LIF signal may be collected orthogonal to the excitation beam using a 50.8 mm diameter f=+100 mm spherical lens 28 and focused onto a 1.5-mm core of a 3 m long fiber 30, such as bundled fiber BFL 1500 from Thorlabs of Newton, N.J., though other lenses and other fibers may be used in other embodiments. The signal may be detected by means of a bandpass filter and a photomultiplier tube (PMT) 32 that is positioned at the other end of the fiber 30. For PLIF measurements the f=+100 mm spherical lens 28 may be replaced with an f=+100 mm, 50.8-mm-square cylindrical lens, thereby generating a laser sheet that approximately 75 mm tall at the probe plane. The PLIF image may be recorded using an ICCD camera in some embodiments.

Embodiments of the fiber-coupled UV-LIF system must meet three criteria: 1) transmission of sufficient laser pulse energy for generation of a LIF signal with reasonable signal-to-noise ratio (SNR) without fiber damage, 2) minimization of beam-profile distortion (i.e., with a smaller beam-quality factor $M^2$), and 3) retention of the spectral and temporal characteristics of the input pulses. Thus, the fiber-delivered excitation-laser beam should have minimal spatial, spectral, and temporal distortions and be tightly focused at the probe volume for making accurate LIF measurements.

Figure 2:
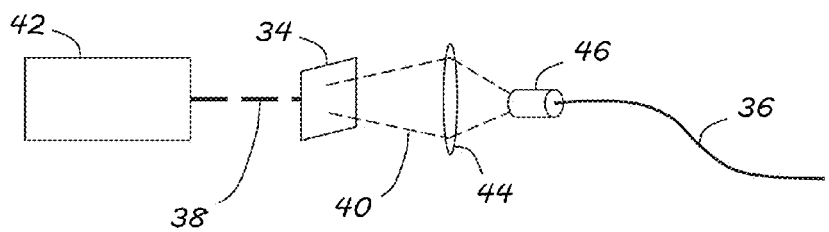
FIG. 2 is a schematic drawing of a high power laser to fiber coupling that may be used with embodiments of the invention such as the apparatus in FIG. 1.

An advance laser-to-fiber coupling method was developed for transmission of higher laser pulse energy through optical fiber to create a larger size laser sheet for expanding PLIF detection area. This coupling method is illustrated in the schematic diagram in FIG. 2. By utilizing a diffractive optical element (DOE) diffuser 34 in conjunction with a designed end-capped fiber 36, the laser-induced damage threshold (LIDT) for the silica fiber may be enhanced by approximately 5-10 fold. The DOE diffuser 34 functions as beam homogenizer to transform a non-uniform laser beam profile 38 into a homogenous beam profile 40, thereby reducing hot spots (within laser 42) generated at a fiber end face and avoiding damage to the fiber surface. The fiber damage threshold may be further improved by coupling the homogenous laser beam output from DOE diffuser 34 to an end-capped fiber 36, using, for example, a lens 44 in some embodiments though other coupling methods may also be used. End caps 46 may be used to protect the end of fiber from environmental damage such as dust.

Figure 3:
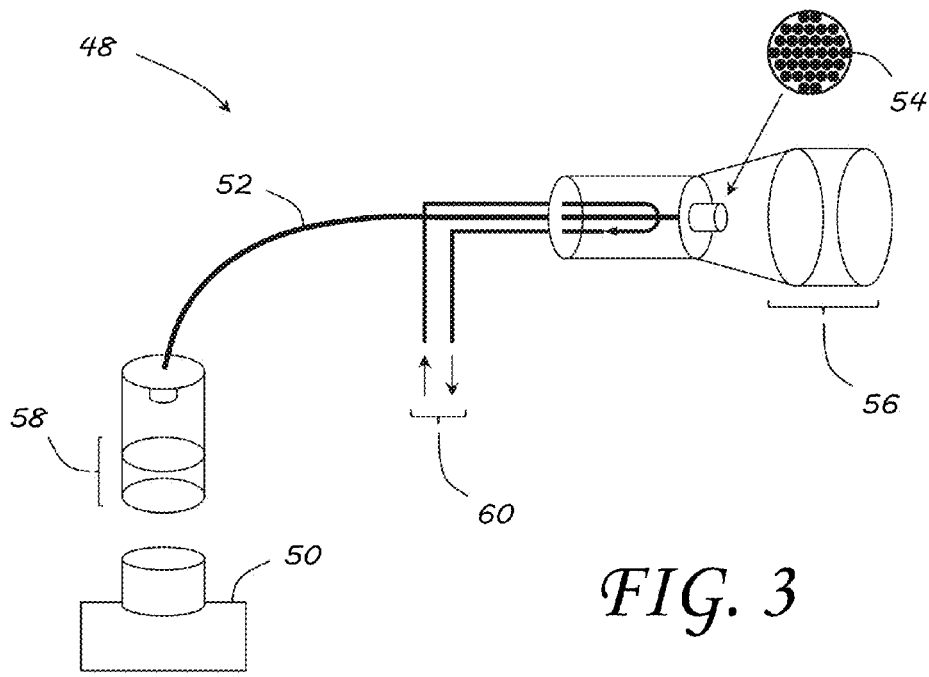
FIG. 3 is a schematic drawing of an imaging fiber bundle design that may be used with embodiments of the invention such as the apparatus in FIG. 1.

An imaging fiberscope probe 48 was also developed for use as an optical probe to collect PLIF imaging signals. The fiberscope probe 48 is designed for direct transmission of high-quality UV PLIF images from the probe volume to a camera 50. This system is based on modern fiber bundles 52 and consists of an array of single mode microfibers arranged in a coherent bundle 54, similar to that shown in FIG. 3, such that the relative position of each fiber remains constant and, hence, a two dimensional image can be transmitted pixel-by-pixel from one end of the fiber bundle 52 to the other. Such imaging fibers are commercially available and consist of individual imaging elements (up to approximately 100,000) in a large-core (approximately 1.5 mm in diameter) fiber bundle. Depending on the dimension of imaging area and the required spatial resolution, an imaging fiber and coupling optics 56, 58 need to be designed. Once a suitable, UV-grade imaging fiber has been selected, it can be integrated into a fiberscope by adding custom micro-optics 56 at the imaging end as well as on the exit plane in front of the ICCD camera. Active cooling 60 (water or air) can be added to the imaging-head assembly containing the integrated micro-optics as well as to the exit end of the fiber or fiber bundle delivering the excitation laser beam. Thermal blanketing (not shown) may also be required for test cell applications where the fiber ends would be exposed to high-temperature environments. The active cooling system may also be added on the launch fiber optics system.

Figure 4:
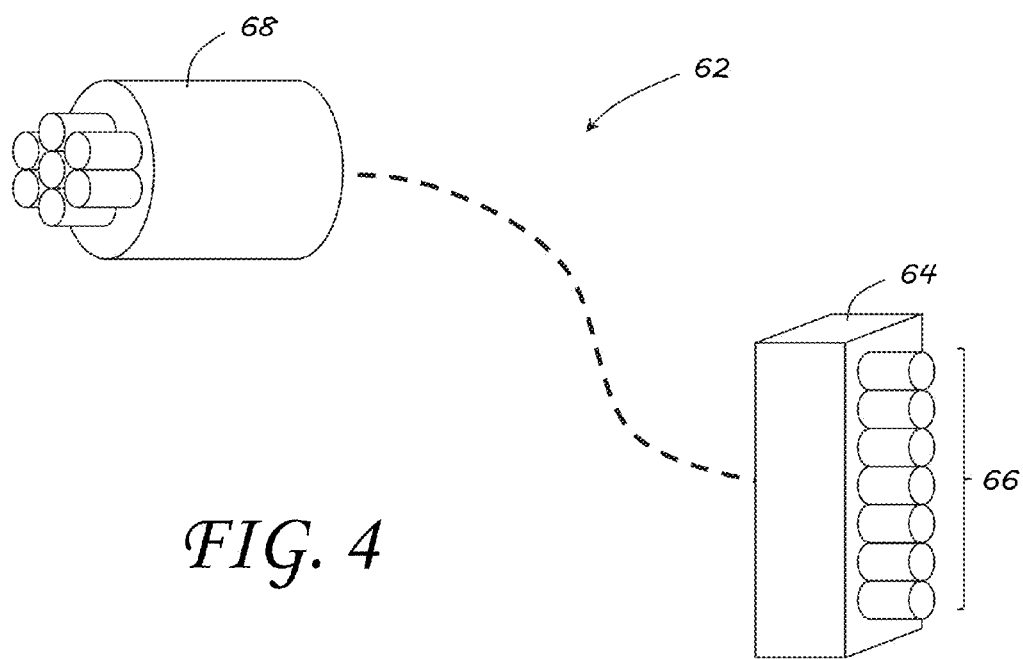
FIG. 4 is an exemplary diagram of fiber bundles that may be configured for two-dimensional PLIF imaging.

A linear fiber array, special fiber bundle design 62, may be utilized for forming a large laser sheet at a test section for large-area PLIF measurements. A sample of the linear-fiber-bundle design is shown in FIG. 4, where an output end of the fiber bundle 64 is formed into a linear array, and the beams may be focused into a sheet using a single cylindrical lens or micro-lenses formed at each fiber end. The fiber optic bundle 62 may be constructed using 7 fused silica step-index fibers 66 with core and cladding diameters of approximately 200 and 220 µm, respectively, though other numbers of fibers and other fiber types may also be used. The materials for the fiber core, cladding, and buffer coating may consist of pure fused silica, doped fused silica, and acrylate, respectively. At an input/output end 68, the individual fibers may be bound together mechanically into a round (linear) bundle for high-power transmission. The design of both the fiberscope imaging system and the linear fiber array may be extended to applications with high temperature and pressure conditions such as combustion chambers, subject to proper shielding of the probes.

Figure 5:
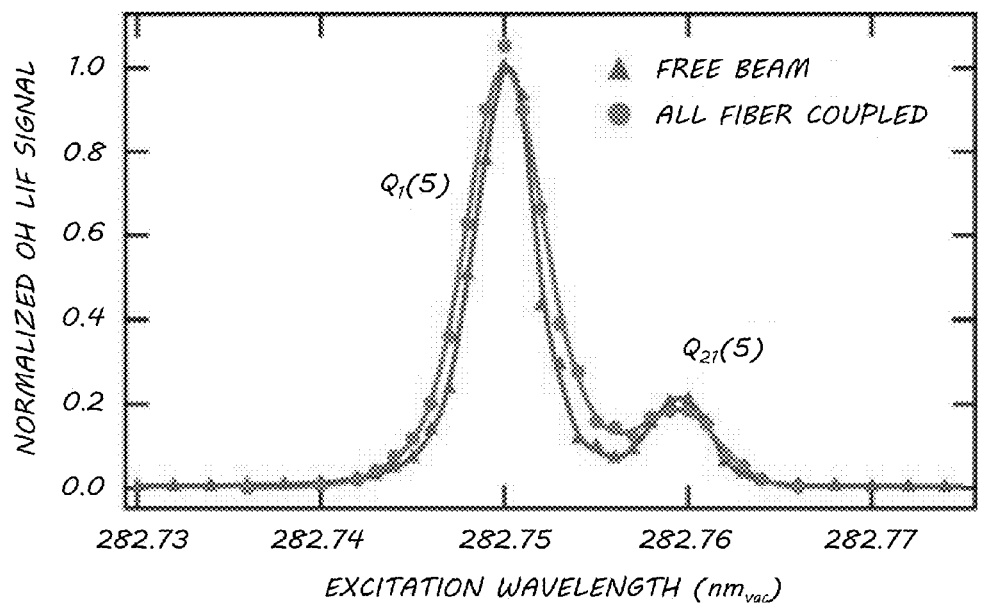
FIG. 5 is a graph of an excitation scan of $Q_1(5)$ and $Q_{21}(5)$ lines with and without fiber coupling.
Figure 6:
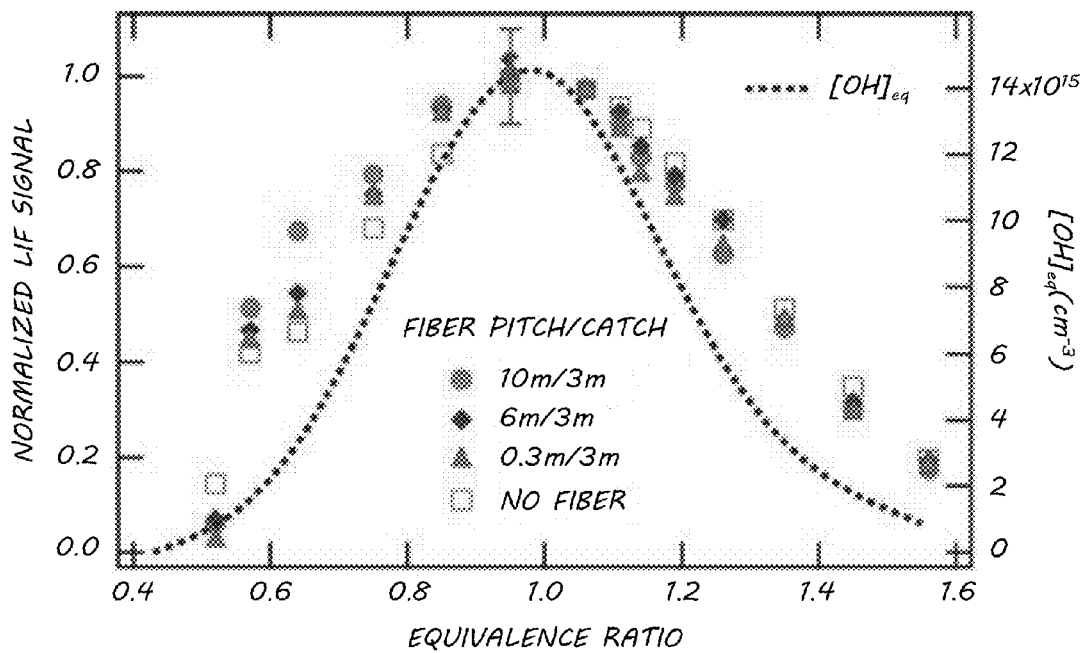
FIG. 6 is a graph of LIF signal as a function of flame equivalence ratio for different lengths of fibers.

Embodiments of the fiber-coupled detection system set forth above were tested and compared with contemporary free beam systems. The results of the comparison are described below. FIG. 5 is an OH-excitation scan recorded by scanning a 10-Hz dye laser over a $Q_1(5)$ and $Q_{21}(5)$ line pair of a (1,0) band of an OH $A^2\Sigma^+$—$X^2\Pi$ system in a $\phi=1.15$ $C_2H_4$/air flame. For both an all-fiber-coupled LIF and a free-beam LIF case, a 50 µJ excitation-pulse energy was employed through a 10 m long fiber and with a signal averaged over 32 laser shots at each step. The resultant signal was normalized by the input laser energy. All acquired OH-LIF profiles were in agreement within the experimental uncertainty, and the effect of fiber delivery on LIF measurement is negligible. Quenching-corrected OH-LIF signals as a function of flame equivalence ratio for a series of $C_2H_4$/air flames are shown in FIG. 6. The excitation-laser energy was 50 µJ, and the signal was averaged over 32 laser shots. All measured OH-LIF profiles were in agreement, within the experimental uncertainty, and no effect of fiber length was observed. Equilibrium flame temperature and species concentrations were calculated using the STANJAN chemical equilibrium code (URL: http://navier.engr.colostate.edu/~dandy/code/code-4/index.html). The equilibrium OH number densities acquired using STANJAN calculations are also shown on the right axis in FIG. 6. Super-equilibrium OH concentrations observed are consistent with previous non-fiber-based OH profiles obtained in this burner by Meyer et al., "Measurements of OH mole fraction and temperature up to 20 kHz by using a diode-laser-based UV absorption sensor," Appl. Opt., Vol. 44, 2005, pp. 6729-6740.

Figure 7:
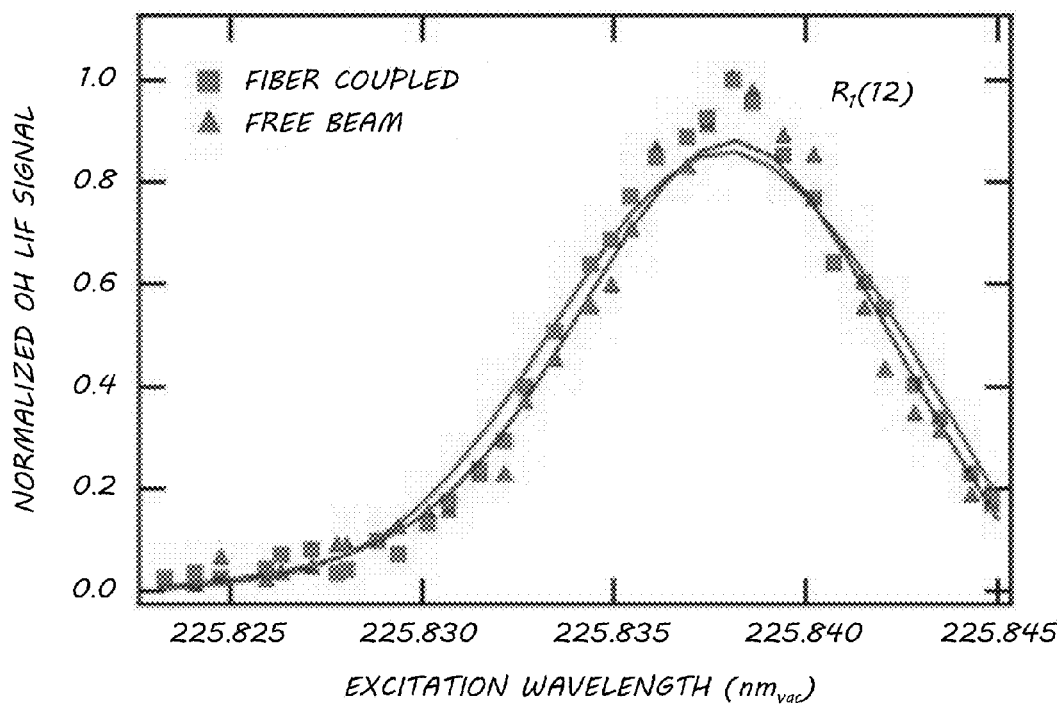
FIG. 7 is a graph of an excitation scan of R1(12) line with and without fiber coupling.

Next, a fiber-coupled UV-LIF system employing a 6-m-long launch fiber is developed for probing NO. FIG. 7 shows the NO-excitation wavelength scan that was recorded by scanning the dye laser over the $R_1(12)$ rotational line of the (0,0) vibrational transition of a $A^2\Sigma^+$—$X^2\Pi_{1/2}$ electronic system. A spectrum acquired by the fiber-based excitation is compared with the free-beam spectrum. For both cases the excitation pulse energy used was approximately 4 µJ, and the signal was averaged over 32 laser shots at each wavelength step. The signal was normalized by the input laser pulse energy at each step. All acquired NO-LIF profiles were in agreement within the experimental uncertainty, and the effect of fiber delivery on LIF measurement is negligible.

A fiber-coupled UV-PLIF system operating at 10-Hz and 10-kHz repetition rate was demonstrated for probing two-dimensional distribution of hydroxyl radicals (OH) in flames and of NO in a room-temperature NO-seeded, N2 jet. For PLIF measurements an f=+100 mm, 50.8 mm square cylindrical lens was applied, thereby generating a laser sheet that was approximately 75 mm tall at the probe plane. The PLIF studies used a $\phi=1.7$ premixed $CH_4/O_2/N_2$ flame having an adiabatic flame temperature of approximately 2,520 K. A PLIF image was recorded by an intensified CCO (ICCO) camera through a 50.8-m-diameter OH bandpass filter. For the images shown in FIGS. 8A and 8B, the excitation beam was delivered through a 400 µm core, 0.3 m long fiber; and the laser-energy output was approximately 400 µJ. The height of the viewing plane was approximately 50 mm, and the laser-beam intensity was nearly uniform in this region; thus, the images shown in FIGS. 8A and 8B are not corrected for spatial energy distribution.

Single laser shot images were also recorded in the same flame using a 10 m long fiber for delivering the laser beam. In this case the maximum energy delivered was limited to approximately 200 µJ, and the output beam diverged approximately two times, as compared to the 0.3-m fiber, resulting in poor spatial resolution. The corresponding single-shot SNR was reduced to approximately 55 µJ as opposed to approximately 200 µJ in the case shown in FIG. 8A. Single-shot and 10-shot-averaged NO-PLIF images of $N_2$/NO gas flows are shown in FIGS. 9A and 9B. The excitation wavelength was around 226.24 nm, and the beam was delivered through a 6-m long FOP fiber. Fluorescence detection was performed using a high-frame-rate CMOS camera and external, two-stage, lens-coupled intensifier. Single-shot PLIF imaging at 10 kHz was acquired for visualizing pulsating turbulent flames. The excitation beam was delivered through a 6-m-long FOP fiber, and the laser-energy output was 12 µJ. The height of the viewing plane was approximately 25 mm, and the laser beam intensity was nearly uniform in this region.

Figure 10A:
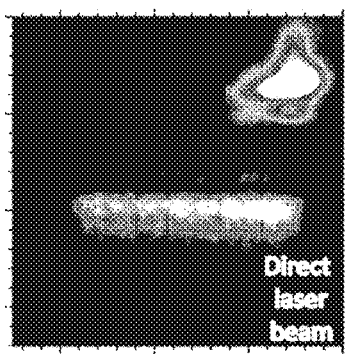
FIGS. 10A and 10B are exemplary 10-averages OH-PLIF images of a $\phi=1.25$ premixed $C_2H_4$-Air Flame in a Henken Burner.
Figure 10B:
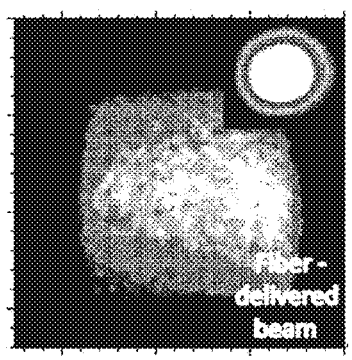

A fiber-coupled PLIF system employing a long-length multimode fiber produces a homogeneous output-beam profile, which may be used for two-dimensional PLIF imaging. As shown in FIGS. 10A and 10B, a high-quality PLIF image was obtained using a fiber-delivered beam with a nearly Gaussian beam profile. A non-uniform spatial beam profile of the UV beam exiting the frequency doubling unit may be transformed to a nearly top-hat profile when transmitted through a long-length, multimode fiber as a result of mode mixing. PLIF images recorded using laser beams delivered through free-standing optics and with fiber delivery through a 6 m long FOP fiber are shown in FIGS. 10A and 10B, respectively. The corresponding spatial beam profiles are also shown in the insets. These results show that laser beam profile homogenization comes as an added advantage of fiber delivery.

While the present invention has been illustrated by a description of one or more embodiments thereof and while these embodiments have been described in considerable detail, they are not intended to restrict or in any way limit the scope of the appended claims to such detail. Additional advantages and modifications will readily appear to those skilled in the art, for transitioning laser diagnostic tools from research laboratories to harsh environments such as those encountered in practical combustor and gas-turbine test facilities. The invention in its broader aspects is therefore not limited to the specific details, representative apparatus and method, and illustrative examples shown and described. Accordingly, departures may be made from such details without departing from the scope of the general inventive concept.

What is claimed is:
1. A high energy UV fiber-coupled laser-induced fluorescence system comprising:
    a transmission component including:
        a laser source configured to produce high-energy UV pulses;
        a first UV-enhanced fused-silica fiber coupled to the laser source; and first optics coupled to the first UV-enhanced fused-silica fiber for transmitting the high-energy UV pulses to a target area; and a receiving component receiving laser-induced florescence events from the target area, the receiving component including:

second optics;

a second UV-enhanced fused-silica fiber coupled to the second optics; and a receiving means coupled to the second UV-enhanced fused-silica fiber.

2. The high energy UV fiber-coupled laser-induced florescence system of claim 1, wherein the receiving means is selected from a group consisting of: a bandpass filter and photomultiplier tube, an ICCD camera, and combinations thereof.

3. The high energy UV fiber-coupled laser-induced florescence system of claim 1, wherein the laser source comprises:

a dye laser.

4. The high energy UV fiber-coupled laser-induced florescence system of claim 3, wherein the laser source further comprises:

a Nd:YAG laser coupled to the dye laser and configured to pump the dye laser.

5. The high energy UV fiber-coupled laser-induced florescence system of claim 4, wherein the laser source further comprises:

a frequency doubler configured to double an output of the dye laser.

6. The high energy UV fiber-coupled laser-induced florescence system of claim 1, wherein the first and second UV-enhanced fused-silica fibers have a length on the order of meters.

7. The high energy UV fiber-coupled laser-induced florescence system of claim 1, wherein the first and second UV-enhanced fused-silica fibers comprise:

a core including a high-purity silica glass which contains OH-groups in the amount of about 0.1 to about 10.0 ppm and chlorine in the amount of less than about 1000 ppm; and a cladding surrounding the core and including a high-purity silica glass which contains fluorine and having a refractive index less than a refractive index of the core.

8. The high energy UV fiber-coupled laser-induced florescence system of claim 7, wherein the first and second UV-enhanced fused-silica fibers are treated in a hydrogen gas to remove intrinsic and impurity defects.

9. The high energy UV fiber-coupled laser-induced florescence system of claim 1, wherein the first UV-enhanced fused-silica fiber is coupled to the laser source by a coupling comprising:

a diffractive optical element diffuser; and a fiber end-cap coupled with the diffractive optical element diffuser.

10. The high energy UV fiber-coupled laser-induced florescence system of claim 9, wherein the first UV-enhanced fused-silica fiber is coupled to the laser source by a coupling further comprising:

a lens, wherein the lens is positioned between the diffractive optical element diffuser and the fiber end cap.

11. The high energy UV fiber-coupled laser-induced florescence system of claim 1, wherein the first UV-enhanced fused-silica fiber comprises:

a plurality of UV-enhanced fused-silica fibers configured as a bundle.

12. The high energy UV fiber-coupled laser-induced florescence system of claim 11, wherein the plurality UV-enhanced fused-silica fibers at an end of the bundle are formed into a linear array.

13. The high energy UV fiber-coupled laser-induced florescence system of claim 11, wherein the receiving component comprises:

a probe coupled to an end of the bundle of the plurality of UV-enhanced fused-silica fibers receiving the laser-induced florescence events from the target area, the probe including:

coupling optics directing the laser-induced florescence events at the plurality of UV-enhanced fused-silica fibers; and active cooling integrated in the probe.

14. The high energy UV fiber-coupled laser-induced florescence system of claim 13, wherein the probe further includes thermal blanketing.

* * * * *